United States Patent [19]

Alila et al.

[11] Patent Number: 5,604,214
[45] Date of Patent: Feb. 18, 1997

[54] REDUCTION OF BOAR ODOR IN MEAT

[75] Inventors: Hector W. Alila, The Woodlands, Tex.;
Michael T. Clark, Downingtown, Pa.;
Richard D. Hedde, West Chester, Pa.;
Mark A. Levy, Wayne, Pa.; Thomas O. Lindsey, Coatesville, Pa.

[73] Assignee: Pfizer Inc., New York, N.Y.

[21] Appl. No.: 513,952

[22] PCT Filed: Mar. 10, 1994

[86] PCT No.: PCT/US94/02600

§ 371 Date: Oct. 20, 1995

§ 102(e) Date: Oct. 20, 1995

[87] PCT Pub. No.: WO94/20112

PCT Pub. Date: Sep. 15, 1994

[30] Foreign Application Priority Data

Mar. 10, 1993 [GB] United Kingdom ............... 9304909

[51] Int. Cl.$^6$ .......................... A61K 31/56; A61K 31/33; A23L 1/31
[52] U.S. Cl. ....................... 514/177; 514/183; 426/574
[58] Field of Search ................... 514/177, 183; 426/574

[56] References Cited

U.S. PATENT DOCUMENTS

| | | | |
|---|---|---|---|
| 3,843,793 | 10/1974 | Gold | 424/324 |
| 4,144,270 | 3/1979 | Neri et al. | 260/562 |
| 4,610,877 | 9/1986 | Pearson et al. | 514/177 |
| 4,760,071 | 7/1988 | Rasmusson et al. | 514/284 |
| 4,954,446 | 9/1990 | Holt et al. | 435/184 |
| 5,017,568 | 5/1991 | Holt et al. | 514/173 |
| 5,372,822 | 12/1994 | Fahim | 424/643 |

OTHER PUBLICATIONS

R. I. Brooks et al., 1986, "Steroid Hormone Pathways in the Pig, with Special Emphasis on Boar Odor: A Review", J. Anim. Sci. 62:632–645.

R. I. Brooks et al., 1986, "An Immunological Approach for Prevention of Boar Odor in Pork", J. Anim. Sci. 62:1279–1289.

Primary Examiner—Raymond Henley, III
Attorney, Agent, or Firm—Peter C. Richardson; Paul H. Ginsburg; Alan L. Koller

[57] ABSTRACT

This invention relates to a method for eliminating or lessening the incidence of boar odor in meat reared from male pigs which comprises administering to such male pigs an effective amount of a boar 4-ene-5-α-reductase inhibiting compound with or without further active ingredients. Also provided is a method for preventing the formation of 5-α-androst-16-en-3-one in male pigs which comprises administering to such male pigs a presently discovered boar 4-ene-5-α-reductase inhibiting compound.

17 Claims, No Drawings

REDUCTION OF BOAR ODOR IN MEAT

This application is a 371 of PCT/US94/02600 filed Mar. 10, 1994.

BACKGROUND OF THE INVENTION

Consumer acceptance of boar meat has been hindered by an objectionable odor in the heated fat of the meat from intact male pigs. Despite the fact that intact male pigs grow faster, utilize feed more efficiently and produce leaner carcasses, castration of male pigs grown for meat production has long been used in commercial practice to eliminate the undesirable odor referred to as "boar odor", "boar taint" or "male sex odor" in pork.

It is generally accepted in the prior art that a family of $5\text{-}\alpha\text{-}C_{19}\text{-}16\text{-en}$ steroids (specifically 5-α-androst-16-en-3-one, 5-α-androst-16-en-3α-ol and 5-α-androst-16-en-3β-ol) are responsible for the objectionable boar odor.

The $5\text{-}\alpha\text{-}C_{19}\text{-}16\text{-en}$ steroids are synthesized in the boar testes by the metabolic pathway shown in FIG. 1 below: Brooks et at., *J. Anim. Sci.* 62 (1986) 632–645.

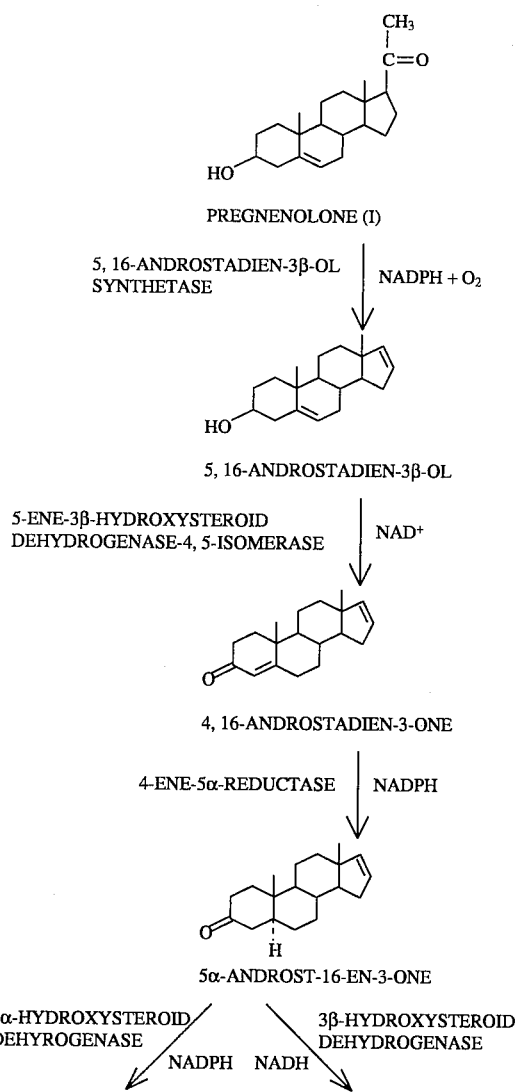

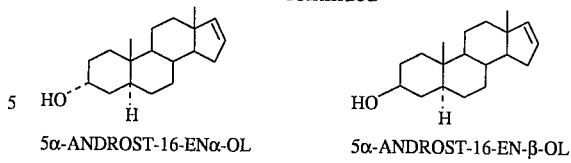

Further, Skatole, a metabolite formed during the breakdown of tryptophan by intestinal microorganisms in pigs, has been found to strengthen synergistically the unpleasand odor of 5-α-androst-16-en-3-one (Lundstrom, et al. *Proc. European Meat. Res. Work* 26:300 (1980)).

Methods for preventing the formation of $5\text{-}\alpha\text{-}C_{19}\text{-}16\text{-en}$ steroids in adult boars, thereby preventing the male sex odor in pork without the need for castration, have concentrated on environment rearing and autoimmunizing young boars against the $5\text{-}\alpha\text{-}C_{19}\text{-}16\text{-en}$ steroids (Brooks, et al, *J. Anim. Sci* 62:632–645 (1986)). Thus far these methods have met with only limited success.

Antibiotics, such as virginiamycin, have demonstrated some efficacy in reducing the level of boar taint by lowering the levels of skatole. (Gadd, *Pigs-Misset* May/June (1992) p17).

With the exception of castration, no reliable method for preventing boar taint in adult male pigs is currently available.

One method of inhibiting boar taint which has to date received virtually no attention is the development of chemical agents which block the production of $5\text{-}\alpha\text{-}C_{19}\text{-}16\text{-en}$ steroids.

Brophy and Gower (*Biochem. Biophys. Acta* 360:252) found that 5-α-pregnane-3,20-dione inhibits the andien-β syntheses system, which is responsible for conversion of pregnenolone to 5, 16-androstadien-3β-ol. However, practical use of 5-α-pregnane-3, 20-doine as an inhibitor of $5\text{-}\alpha\text{-}C_{19}\text{-}16\text{-en}$ steroid formation is not feasible because it simultaneously inhibits formation of androgenic and estrogenic sex hormones elsewhere in the biosynthetic pathway of steroidal hormones in the boar. The use of chemical agents to prevent the conversion of 17β-hydroxy-3-oxoandrost-4-ene to 17β-hydroxy-5-α-androst-3-one by inhibiting the activity of steroid 5-α-reductase in rats, dogs and humans has been examined (Liang, et al. *Endocrinology*, 117, No. 2, 571–579 (1985)) (hereinafter Liang, et al.). Liang concluded that there are significant differences between the rat, dog and human forms of 5-α-reductase thereby emphasising the nontransferability of an agent's inhibitory potential of this enzyme between species. To date no successful method of chemically inhibiting the boar 4-ene-5-α-reductase enzyme, thereby preventing the in vivo conversion of 4,16-androstadien-3-one to 5-α-androst-16-en-3-one, has been reported.

The development of a suitable chemical-blocking agent to prevent formation of the boar $5\text{-}\alpha\text{-}C_{19}\text{-}16\text{-en}$ steroids without inhibiting production of 4-ene androgenic and estrogenic sex hormones would be extremely valuable. Preferably such chemical-blocking agent will prevent the formation of 5-α-androst-16-en-3-one so that subsequent reduction to the α-ol and β-ol forms are also prevented.

SUMMARY OF THE INVENTION

This invention relates to a method for eliminating or lessening the incidence of boar odor in meat from reared male pigs which comprises administering to such male pigs an effective amount Of a boar 4-ene-5-α-reductase inhibiting compound.

This invention also relates to a method for preventing the formation of 5-α-androst-16-en-3-one in male pigs which comprises administering to such male pigs a boar 4-ene-5-α-reductase inhibiting compound. Included in the present invention are methods for eliminating or lessening the incidence of boar odor in meat from reared male pigs which comprises the co-administration of a boar 4-ene-5-α-reductase inhibiting compound with further active ingredients.

DETAILED DESCRIPTION OF THE INVENTION

The term "virginiamycin" as used herein refers to an antibiotic obtained from streptomyces virginiae. Virginiamycin is marketed commercially for use in the treatment and control of swine dysentery and for improving growth rate and feed utilization efficiency.

A preferred compound for use in the presently invented methods -17β-(N-t-butylcarboxamide)-androst-3,5-diene-3-carboxylic acid—and processes to prepare said compound are disclosed and claimed in U.S. Pat. No. 5,017,568, the entire disclosure of which is hereby incorporated by reference.

A preferred compound for use in the presently invented methods—17β-(N-t-butylcarboxamide)-estr-1,3,5(10)triene-3-carboxylic acid—and processes to prepare said compound are disclosed and claimed in U.S. Pat. No. 4,954,446, the entire disclosure of which is hereby incorporated by reference.

A preferred compound for use in the presently invented methods—17β-(N-t-butylcarbamol)-4-aza-5-α-androst-1-en-3-one- and processes to prepare said compound are described in and said compound is claimed in U.S. Pat. No. 4,760,071, the entire disclosure of which is hereby incorporated by reference.

Nothing in the cited patents discloses or suggest that the above-referenced compounds or any compound disclosed therein would have utility in eliminating or lessening the incidence of boar odor in meat from reared male pigs.

It has now been discovered, for the first time, that the boar 4-ene-5-α-reductase enzyme responsible for converting 4,16-androstadiene-3-one to 5-α-androst-16-en-3-one (which is subsequently reduced in the boar to the 3α-ol and 3β-ol forms) can be inhibited by compounds within the scope of this invention.

The preferred compounds of this invention (i.e. 17β-(N-t-butylcarboxamide)-androst-3,5-diene-3-carboxylic acid, 17β-(N-t-butylcarboxamide)-estr-1,3,5(10)triene-3-carboxylic acid and 17β-(N-t-butylcarbamoyl)-4-aza-5α-androst-1-en-3-one) were tested for their potency in inhibiting the boar 4-ene-5-α-reductase enzyme, using the procedure described below.

Microsomal preparations from boar salivary glands were prepared by the protocol desbribed by Liang, et al. for human prostatic microsomal 5-α-reductase.

Assay for enzyme activity and inhibitor potency.

A constant amount of [$^{14}$C]testosterone (50 to 55 mCi/mmol) in ethanol and varying amounts of potential inhibitor (or no inhibitor i.e. control) in ethanol were deposited in test tubes and concentrated to dryness in vacuo. Assays for boar steroid 5α-reductase enzyme were conducted with a sample of the boar salivary gland 5-α-reductase in 50 mM phosphate buffer, pH 7.5 or in 50 mM citrate buffer at pH 5.0. To each tube was added buffer, 40 µl of microsomal preparation from boar salivary glands (hereinafter boar salivary gland steroid 5-α-reductase) and 20 µl of 20 mM NADPH to a final volume of 0.5 mL.

After incubating the solution at 37° C. for 30 minutes the reaction was quenched by the addition of 4 mL ethyl acetate and 0.25 µmol each of testosterone, 5α-dihydrotestosterone, androstanediol, and androstanedione as carriers. The organic layer was removed to a second test tube and evaporated to dryness in a Speed Vac. The residue was dissolved in 40 µL chloroform, spotted on an individual lane of a 20×20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan Inc., Washington, D.C.). The percent of recovered radiolabel converted to product was calculated, from which enzyme activity was determined. All incubations were conducted such that no more than 20% of the substrate (testosterone) was consumed.

By following the above procedure in the absence of an inhibitor (i.e. control) a significant formation of 5-α-dihydrotestosterone, and the androstanediols occurred which indicated the presence of a high level of 4-ene-5-α-reductase enzyme activity in the microsomes prepared from the salivary glands of the boar.

By way of comparison, 500 nM of 17δ(N-t-butylcarbamoyl)-4-aza-5-α-androst-1-en-3-one and 500 nM of 17β-(N-t-butylcarboxamide)-androst-3,5-diene-3-carboxylic acid each individually caused 30 to 40% inhibition of the boar 5-α-reductase enzyme at pH 5 (vs. control) and 50% inhibition of the boar 5-α-reductase enzyme at pH 7.5 (vs. control). 500 nM of 17β-(N-t-butyl carboxamide)-estr-1,3,5(10)triene-3-carboxylic acid caused about a 65% inhibition of the boar 5-α-reductase enzyme at pH 5 (vs. control) and 80% inhibition of the boar 5-α-reductase enzyme at pH 7.5 (vs. control).

Compounds other than 17β(N-t-butylcarboxamoyl)-4-aza-5-α-androst-1-en-3-one, 17β-(N-t-butylcarboxamide)-androst-3,5-diene-3carboxylic acid and 17β-(N-t-butylcarboxamide)-estr-1,3,5(10)triene-3-carboxylic acid and which have utility as potent inhibitors of the boar 4-ene-5-α-reductase enzyme will demonstrate an inhibitory effect in the above assay. All such compounds are included in the term "boar 4-ene-5-α-reductase inhibiting compound" as used herein and are included within the scope of the methods of this invention.

Because compounds within the scope of this invention inhibit the boar 4-ene-5-α-reductase enzyme, they have utility in preventing the formation of 5-α-androst-16-en-3-one in reared male pigs. Because the presence of 5-α-androst-16-en-3-one (which is subsequently reduced to the corresponding 3α-ol and 3β-ol forms in vivo) is associated with boar mint, compounds within the scope of this invention are useful in eliminating or reducing the incidence of boar taint. The method of this invention is particularly useful in that, by inhibiting the boar 4-ene-5-α-reductase enzyme the formation of 4-ene androgenic and estrogenic sex hormones in the boar are unaffected.

The invention also provides for the use of a boar 4-ene-5-α-reductase inhibiting compound in the manufacture of a medicament for use in eliminating or lessening the incidence of boar taint.

The invention also provides for a pharmaceutical or veterinary composition for use in eliminating or lessening the incidence of boar taint which comprises a boar 4-ene- 5-α-reductase inhibiting compound and a pharmaceutically acceptable carrier.

By the term "effective amount" as used herein, is meant that a boar 4-ene-5-α-reductase inhibiting compound (active compound) is administered to a boar in an amount sufficient to reduce the accumulation of 5-α-$C_{19}$-16-en steroids in the boar to acceptable levels. Said acceptable levels being sufficient to eliminate or to lessen the incidence of male sex odor from the meat of a boar so treated.

While it is possible for a boar 4-ene-5-α-reductase inhibiting compound to be administered alone, it is preferable to present said compound as a salt, hydrate, solvate, in a preparation or as an admixture.

Compounds within the scope of the present invention are preferably incorporated into convenient dosage forms such as capsules, implants, tablets, injectable preparations or feed admixtures. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, a carrier or diluent may include any prolonged release material, such as glyceryl monostearate or glyceryl distearate, alone or with a wax. The mount of solid carrier varies widely but, preferably, will be from about 25 mg to about 1 g per dosage unit. When a liquid carrier is used, the preparation will be preferably in the form of a syrup, elixir, emulsion, soft gelatin capsule, sterile injectable liquid such as an ampoule, or an aqueous or nonaqueous liquid suspension.

The admixtures and preparations are made following conventional techniques involving mixing, granulating, and compressing, when necessary, for tablet forms, or mixing, filling and dissolving the ingredients, as appropriate, to give the desired oral or parenteral products.

Doses of the compounds within the scope of this invention will be an efficacious, non-toxic quantity preferably selected from the range of 0.1–2500 mg/kg of active compound preferably 1–250 mg/kg. The selected dose is administered to male pigs preferably from 1–6 times daily, orally or parenterally prior to slaughter. Preferred forms of parenteral administration include topically, by implant, transdermally and by injection. Oral administration is preferably preformed by way of a feed additive. Active compound would be included in feed at levels from 25–2500 mg/kg. Dosage units for boar administration preferably contain from 1 to 10,000 mg of active compound.

Because compounds within the scope of this invention prevent formation of 5-α-$C_{19}$-16-en steroids in the boar without inhibiting the formation of androgenic and estrogenic sex hormones the administration of a boar 4-ene-5-α-reductase inhibiting compound (as described herein) can commence in young boars, prior to sexual maturity, to prevent formation of the 5-α-$C_{19}$-16-en steroids or in sexually mature boars to reduce the level of 5-α-$C_{19}$-16-en steroids below odor causing levels prior to slaughter.

Methods for rapid identification of skatole in tainted boar carcass after slaughter are known in the art (Gadd, *Pigs Missed* May/June (1992) p17). Taint caused by androstenone can be measured as described by Bonneau, et al. *Livestock Production Science* 32 (1992) 63–80 p66. As such, it will be recognized by one of skill in the art that the optimal quantity and spacing of individual dosages of a boar 4-ene-5-α-reductase inhibiting compound needed to assure that the accumulation of 5-α-$C_{19}$-16-en steroids in the boar is at such a level as to eliminate or lessen the incidence of boar taint can be determined by routine testing using conventional techniques.

As used herein, when a boar 4-ene-5-α-reductase inhibiting compound and a further active ingredient are utilized in combination, said inhibitor can be co-administered with said further active ingredient.

By the term "co-administering" and derivatives thereof as used herein is meant either simultaneous administration or any manner of separate sequential administration of a boar 4-ene-5-α-reductase inhibiting compound and a further active ingredient, such as other compounds known to eliminate or lessen the incidence of boar odor in the meat from reared male pigs. Exemplary of further active ingredients as used herein includes, antibiotics and immunisation with antibodies. Particularly preferred is a combination of an inhibitor of boar 4-ene-5-α-reductase and virginiamycin for use in eliminating boar taint. Simultaneous administration may be in the form of a single composition. Preferably, if the administration is not simultaneous, the two compounds are administered in a close time proximity to each other. Furthermore, it does not matter if the compounds are both administered in the same dosage form, e.g. one compound may be administered by injection and the other compound may be administered orally.

This invention also relates to the meat from male pigs treated using the method according to the invention, which meat is suitable for human consumption as it lacks the boar odor.

No unacceptable toxicological effects are expected when compounds of the invention are administered in accordance with the present invention.

Without further elaboration, it is believed that one skilled in the art can, using the preceding description, utilize the present invention to its fullest extent. The following examples are, therefore, to be construed as merely illustrative and not a limitation of the scope of the present invention in any way.

EXAMPLE 1 - CAPSULE COMPOSITION

An oral dosage form for administering boar 4-en-5-α-reductase inhibiting compounds is produced by filing a standard two piece hard gelatin capsule with the ingredients in the proportions shown in Table I, below.

TABLE I

| INGREDIENTS | AMOUNTS |
| --- | --- |
| N-t-butyl-estr-1,3,5(10)-triene-17β-carboxamide-3-carboxylic acid | 25 mg |
| Lactose | 55 mg |
| Talc | 16 mg |
| Magnesium Stearate | 4 mg |

EXAMPLE 2 - INJECTABLE PARENTERAL COMPOSITION

An injectable form for administering boar 4-en-5-α-reductase inhibiting compounds is produced by stirring 1.5% by weight of N-t-butyl-estr-1,3,5(10)-triene-17β-carboxamide-3-carboxylic acid in 10% by volume propylene glycol in water.

EXAMPLE 3 - FEED ADDITIVE

The sucrose, calcium sulfate dihydrate and boar 4-en-5-α-reductase inhibiting compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
|---|---|
| N-t-butyl-estr-1,3,5(10)-triene-17β-carboxamide-3-carboxylic acid | 20 mg |
| calcium sulfate dihydrate | 30 mg |
| sucrose | 4 mg |
| starch | 2 mg |
| talc | 1 mg |
| stearic acid | 0.5 mg |

EXAMPLE 4 -FEED ADDITIVE

A feed additive from for administering boar 4-ene-5-α-reductase inhibiting compound is produced by mixing in the boar feed 0.0025% by weight of N-t-butyl-estr-1,3,5(10)triene-17β-carboxamide-3-carboyxlic acid.

EXAMPLE 5 - FEED ADDITIVE

Virginiamycin and N-t-butyl-estr-1,3,5(10)-triene-17β-carboramide-3-carboxylic acid are formed into a premix. The premix is then added to form a complete feed mix by the farmer or feed compounder. The premix is added at the rate of 1000 grams per 1000 kg of feed.

| Ingredients | Amounts |
|---|---|
| N-t-butyl-estr-1,3,5(10)-triene-17β-carboxamide-3-carboxylic acid | 20 g |
| virginiamycin | 10 g |
| lactose | 500 g |
| starch | 430 g |
| peanut oil | 40 g |
| | 1000 grams premix |

While the above descriptions and examples fully describe the invention and the preferred embodiments thereof, it is understood that the invention is not limited to the particular disclosed embodiments coming within the scope of the following claims.

What is claimed is:

1. A method for eliminating or lessening the incidence of "boar odor" in meat from reared male pigs which comprises administering to such male pigs an effective amount of a boar 4-ene-5-α-reductase inhibiting compound.

2. The method of claim 1 in which the boar 4-ene-5-α-reductase inhibiting compound is administered parenterally.

3. The method of claim 2 in which from about 0.1 mg/kg to about 2500 mg/kg of compound is administered per day.

4. The method of claim 1 in which the boar 4-ene-5-α-reductase inhibiting compound is administered orally.

5. The method of claim 4 in which from about 0.1 mg/kg to about 2500 mg/kg of compound is administered per day.

6. The method of claim 1 in which the boar 4-ene-5-α-reductase inhibiting compound is;

17β(N-t-butylcarboxamide)-androst-3,5-diene-3-carboxylic acid,

17β-(N-t-butylcarboxamide)-estr-1,3,5(10)triene-3-carboxylic acid or

17β-(N-t-butylcarbamoyl)-4-aza-5-α-androst-1-en-3-one.

7. A method for preventing the formation of 5-α-androst-16-en-3-one in male pigs which comprises administering to such male pigs a boar 4-ene-5-α-reductase inhibiting compound.

8. The method of claim 7 in which the boar 4-ene-5-α-reductase inhibiting compound is administered parenterally.

9. The method of claim 8 in which from about 0.1 mg/kg to about 2500 mg/kg of compound is administered per day.

10. The method of claim 7 in which the boar 4-ene-5-α-reductase inhibiting compound is administered orally.

11. The method of claim 10 in which from about 0.1 mg/kg to about 2500 mg/kg of compound is administered per day.

12. The method of claim 7 in which the boar 4-ene-5-α-reductase inhibiting compound is 17β(N-t-butylcarboxamide)-androst-3,5-diene-3-carboxylic acid, 17β-(N-t-butylcarboxamide)-estr-1,3,5(10)triene-3-carboxylic acid or 17β-(N-t-butylcarbamoyl)-4-aza-5-α-androst-1-en-3-one.

13. A method of eliminating or lessening the incidence of "boar odor" in meat from reared male pigs which comprises separate sequential or simultaneous administration of a boar 4-ene-5-α-reductase inhibiting compound and a further active ingredient.

14. The method of claim 13 in which the further active ingredient is virginiamycin.

15. A composition for eliminating or lessening the incidence of boar taint, comprising an effective amount of a boar 4-ene-5-α-reductase inhibiting compound and virginiamycin.

16. The composition of claim 15 in which the boar 4-ene-5-α-reductase inhibiting compound is 17β-(N-t-butylcarboxamide)-estr-1,3,5(10)triene-3-carboxylic acid.

17. Boar meat obtained by a process comprising the steps of:

(a) treating a boar by administering an effective amount of a boar 4-ene-5-αreductase inhibiting compound to obtain a boar having reduced odor; and (b) slaughtering said boar having reduced odor, wherein the formation of 4-ene androgenic and estrogenic sex hormones in said boar are unaffected.

* * * * *